US012374451B2

(12) United States Patent
Kaneria et al.

(10) Patent No.: US 12,374,451 B2
(45) Date of Patent: Jul. 29, 2025

(54) AUTOMATED DEVICE EFFICACY DETERMINATION SYSTEMS FOR HEALTH MONITORING DEVICES

(71) Applicant: Express Scripts Strategic Development, Inc., St. Louis, MO (US)

(72) Inventors: Ankur Kaneria, Cedar Park, TX (US); Harry S. Gangaikondan-Iyer, Morris Plains, NJ (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 306 days.

(21) Appl. No.: 17/994,996

(22) Filed: Nov. 28, 2022

(65) Prior Publication Data

US 2023/0085903 A1    Mar. 23, 2023

Related U.S. Application Data

(62) Division of application No. 17/072,609, filed on Oct. 16, 2020, now Pat. No. 11,515,035.

(51) Int. Cl.
| | |
|---|---|
| *G16H 40/60* | (2018.01) |
| *G06F 21/62* | (2013.01) |
| *G16H 40/40* | (2018.01) |
| *G16H 50/30* | (2018.01) |

(52) U.S. Cl.
CPC ......... *G16H 40/60* (2018.01); *G06F 21/6245* (2013.01); *G16H 40/40* (2018.01); *G16H 50/30* (2018.01)

(58) Field of Classification Search
None
See application file for complete search history.

(56) References Cited

U.S. PATENT DOCUMENTS

| | | | |
|---|---|---|---|
| 9,782,075 | B2 | 10/2017 | Redei |
| 10,116,616 | B2 | 10/2018 | Savenok |
| 10,332,639 | B2 | 6/2019 | Smurro |
| 10,484,376 | B1 | 11/2019 | Laucius |

(Continued)

FOREIGN PATENT DOCUMENTS

| | | |
|---|---|---|
| EP | 3563596 A | 11/2019 |
| EP | 3606123 A1 | 2/2020 |

(Continued)

*Primary Examiner* — Scott B Christensen
(74) *Attorney, Agent, or Firm* — Miller Johnson

(57) ABSTRACT

A computerized method of capturing monitor device data in a blockchain includes receiving a product identifier and product registration information for a monitor device supplied by a vendor. The method includes generating a secret device key for the monitor device. The method includes configuring the monitor device with the secret device key. The method includes receiving a member identifier and member registration information for a member associated with the monitor device. The method includes generating, by a blockchain secret member key ledger, a secret member key. The method includes linking the secret member key with the monitor device. The method includes receiving, by a blockchain secret member-device association ledger, an associated pair of the secret device key with the secret member key to store the associated pair for further authentication and authorization by the blockchain secret member-device association ledger.

20 Claims, 12 Drawing Sheets

(56) References Cited

U.S. PATENT DOCUMENTS

| | | |
|---|---|---|
| 10,540,640 B1 | 1/2020 | James |
| 10,547,594 B2 | 1/2020 | Chang |
| 10,660,522 B2 | 5/2020 | Redei |
| 2004/0215981 A1* | 10/2004 | Ricciardi ............... G16H 50/30 713/176 |
| 2013/0275612 A1 | 10/2013 | Voss |
| 2015/0019273 A1 | 1/2015 | Grosz |
| 2015/0194146 A1 | 7/2015 | Wu |
| 2016/0125149 A1 | 5/2016 | Abramowitz |
| 2016/0125170 A1 | 5/2016 | Abramowitz |
| 2017/0232300 A1* | 8/2017 | Tran ....................... G06F 1/163 434/247 |
| 2018/0294047 A1 | 10/2018 | Hosseini |
| 2018/0358117 A1 | 12/2018 | Neagle |
| 2019/0058697 A1 | 2/2019 | Chang |
| 2019/0206564 A1 | 7/2019 | Shelton, IV |
| 2019/0214113 A1 | 7/2019 | Abramowitz |
| 2019/0221303 A1 | 7/2019 | Bennett |
| 2019/0228847 A1 | 7/2019 | Soli |
| 2019/0236286 A1* | 8/2019 | Scriber ............... H04L 63/0435 |
| 2019/0238525 A1* | 8/2019 | Padmanabhan ....... H04L 63/101 |
| 2019/0349261 A1 | 11/2019 | Smith |
| 2019/0355483 A1 | 11/2019 | Smurro |
| 2019/0392928 A1 | 12/2019 | Hosseini |
| 2020/0005912 A1* | 1/2020 | Saliman ................. G16H 20/00 |
| 2020/0013050 A1 | 1/2020 | Finlow-Bates |
| 2020/0019995 A1 | 1/2020 | Krishnan |
| 2020/0118127 A1 | 4/2020 | Miller |
| 2020/0185095 A1 | 6/2020 | Miller |
| 2020/0202989 A1* | 6/2020 | Dror ...................... G16H 30/20 |
| 2020/0210647 A1 | 7/2020 | Panuganty |
| 2020/0243180 A1 | 7/2020 | Wamburu |
| 2020/0281469 A1 | 9/2020 | Redei |
| 2020/0334229 A1* | 10/2020 | Harrison .................. A61G 7/05 |
| 2021/0311864 A1 | 10/2021 | Gottlieb |

FOREIGN PATENT DOCUMENTS

| | | |
|---|---|---|
| IN | 201741013738 | 10/2018 |
| JP | 2019526120 A | 9/2019 |
| TW | 201810151 A | 3/2018 |
| WO | 2018126075 A1 | 7/2018 |
| WO | 20181626871 A1 | 9/2018 |
| WO | 20190360191 A1 | 2/2019 |
| WO | 20190798901 A1 | 5/2019 |
| WO | 20192229041 A1 | 11/2019 |

* cited by examiner

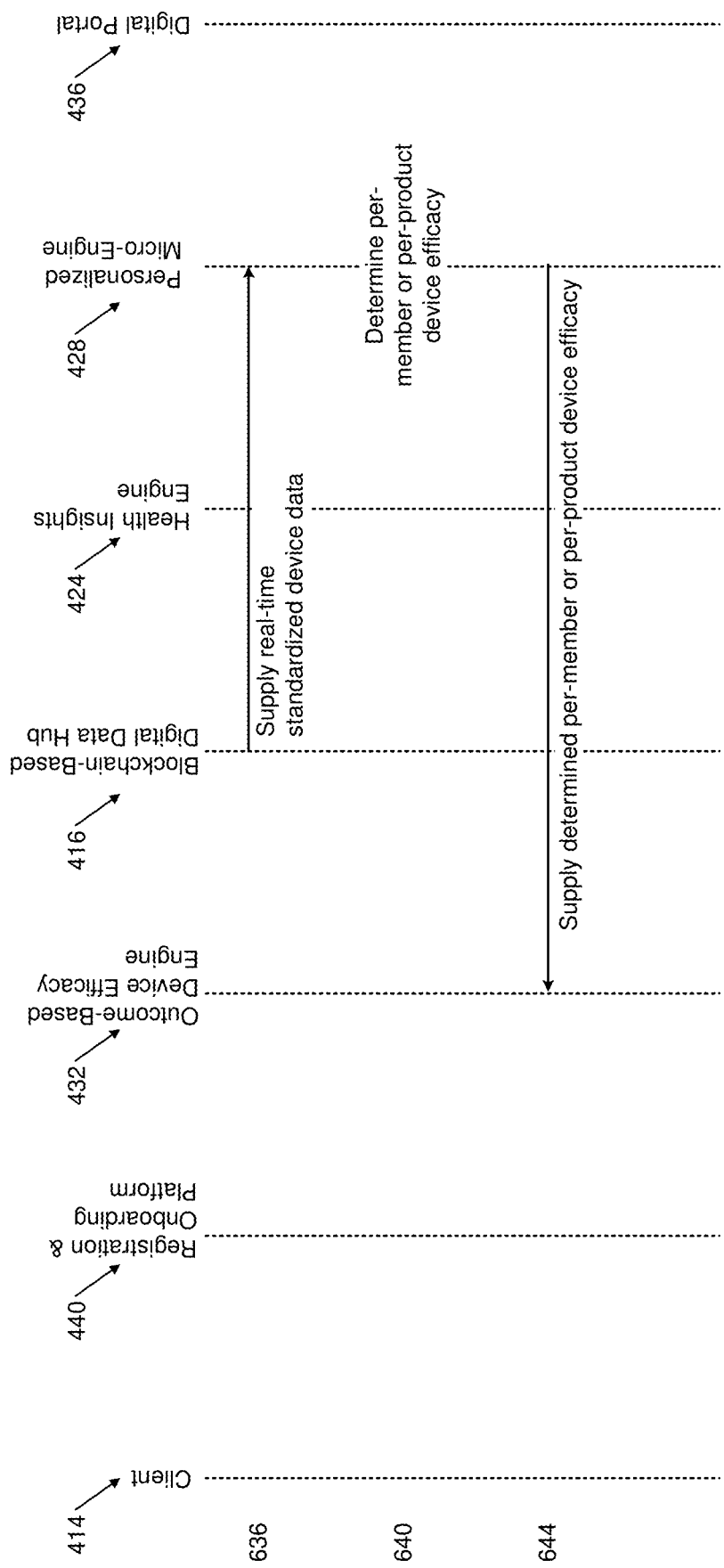

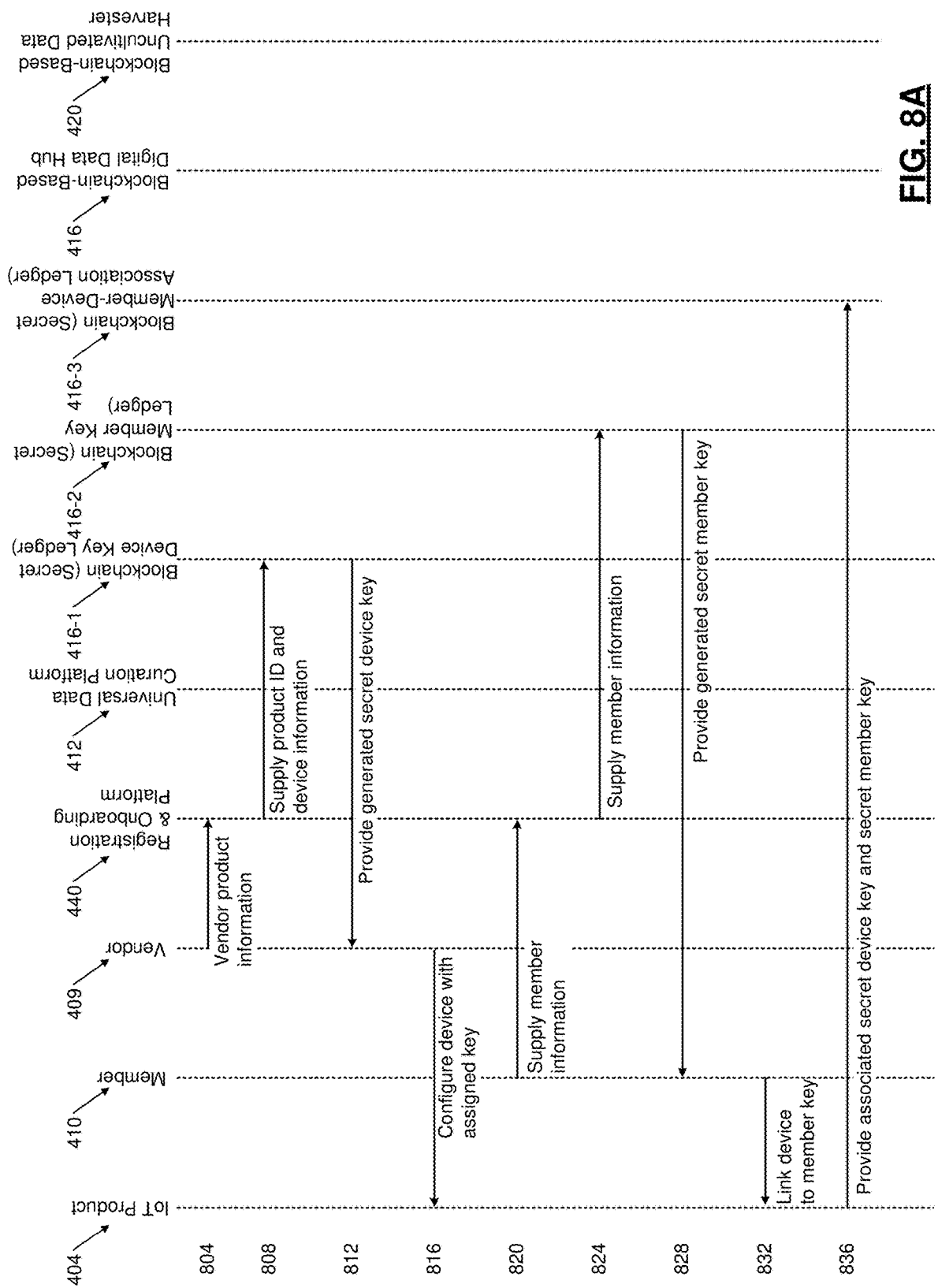

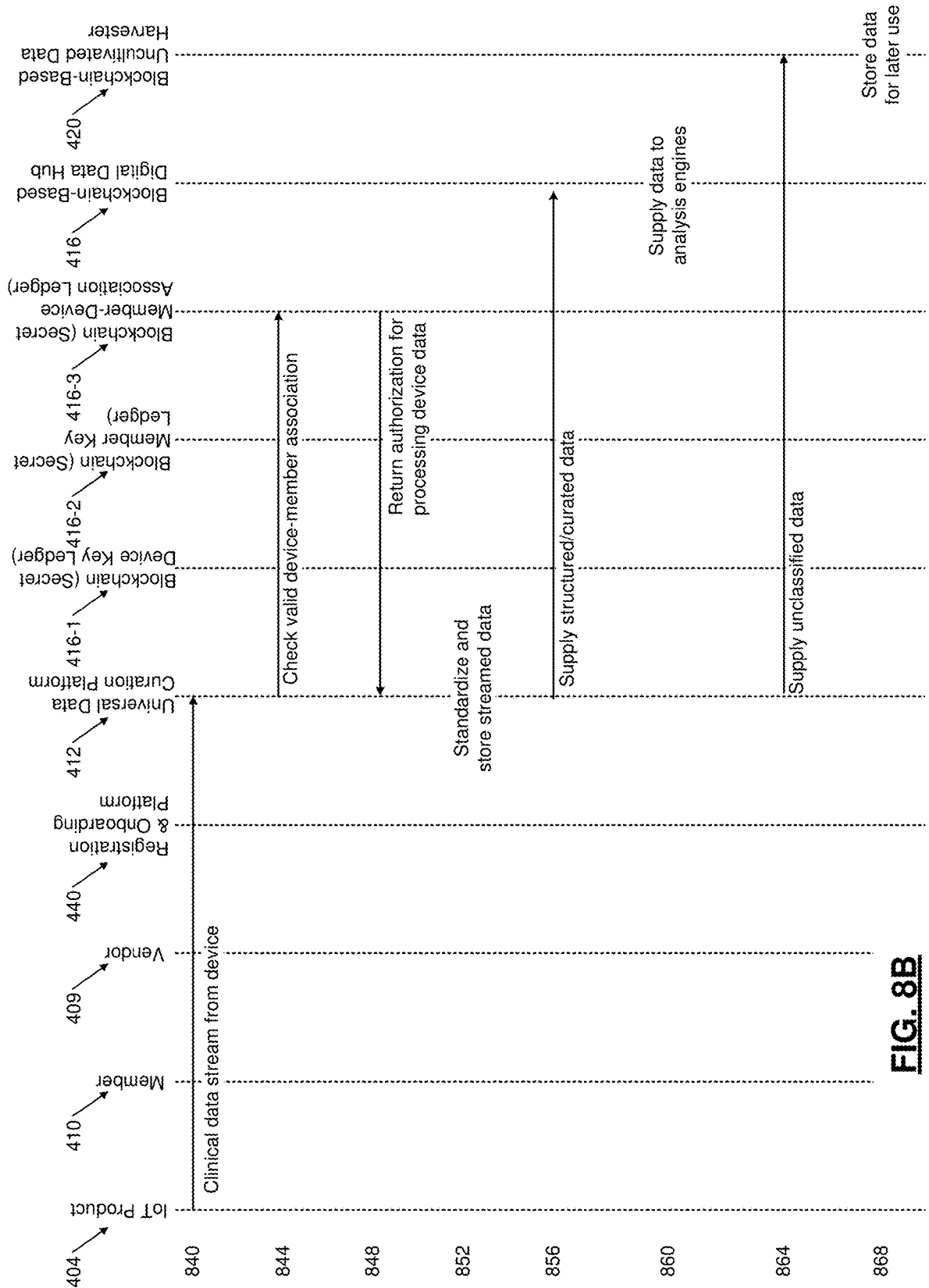

even number: US 12,374,451 B2

AUTOMATED DEVICE EFFICACY DETERMINATION SYSTEMS FOR HEALTH MONITORING DEVICES

CROSS-REFERENCE TO RELATED APPLICATIONS

This application is a divisional of U.S. patent application Ser. No. 17/072,609, filed Oct. 16, 2020 (now U.S. Pat. No. 11,515,035). This application is related by subject matter to U.S. patent application Ser. No. 17/072,693, filed Oct. 16, 2020. The entire disclosures of the above applications are incorporated by reference.

FIELD

The present disclosure relates to health monitoring devices and more particularly to automated device efficacy systems for health monitoring devices.

BACKGROUND

Product vendors offer a variety of Internet-of-things (IoT) devices for tracking health aspects of users, including smart watches, fitness trackers, smartphones, blood glucose monitors, blood pressure monitors, etc. Product vendors may also store data for users in cloud-based systems. Data from the devices and/or cloud-based systems may be streamed to computing devices to be reviewed by the users, and the streaming data often includes raw and noisy data streams, incomplete data, etc. Streaming data from disparate devices and vendors may have many different formats.

Separately, client organizations, such as a pharmacy, a hospital, a healthcare provider, a corporation, etc., may offer programs for its members that encourage the members to use health monitoring devices to improve the health of the members, reduce healthcare costs for the members, etc. For example, product vendors may reach out to client organizations to advertise expected benefits of the members using device(s) of the product vendor.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computer system includes memory configured to store computer-executable instructions and a universal data curation platform including multiple device profiles, each device profile including multiple fields for storing received device attributes in a standardized format. The system also includes at least one processor configured to execute the instructions. The instructions include registering a first monitor device supplied by a first vendor, associating the first monitor device with a first member, registering a second monitor device supplied by the first vendor or a second vendor, associating the second monitor device with the first member or a second member, and receiving streaming health data from the first monitor device and the second monitor device, the received streaming health data including multiple data values sensed by the first monitor device and the second monitor device. The instructions include identifying, by the universal data curation platform, a first one of the multiple device profiles corresponding to the first monitor device, and transforming and storing the multiple data values sensed by the first monitor device into the standardized format device attributes of the identified device profile corresponding to the first monitor device. The instructions include identifying, by the universal data curation platform, a second one of the multiple device profiles corresponding to the second monitor device, and transforming and storing the multiple data values sensed by the second monitor device into the standardized format device attributes of the identified device profile corresponding to the second monitor device. The instructions include supplying the stored standardized format device attributes to at least one data analysis engine to determine one or more health characteristics of at least one of the first member and the second member.

In other features, the standardized format device attributes include at least one of a device measurement value, a measurement type, a measurement timestamp, and a member identifier. In other features, the universal data curation platform comprises a hidden data layer including a data rationalization engine and multiple hidden layer nodes, receiving the streaming health data includes receiving multiple data packets from the first monitor device and the second monitor device at an external data layer, transforming and storing the multiple data values sensed by the first monitor device includes mapping data packets received from the first monitor device to the hidden layer nodes associated with the identified device profile corresponding to the first monitor device, and transforming and storing the multiple data values sensed by the second monitor device includes mapping data packets received from the second monitor device to the hidden layer nodes associated with the identified device profile corresponding to the second monitor device.

In other features, the instructions further include identifying, by the data rationalization engine, noise values in the streaming health data, and inhibiting storing of the noise values in the multiple hidden layer nodes of the hidden data layer. In other features, the hidden data layer of the universal data curation platform includes a data harvest engine, and supplying the stored standardized format device attributes includes mapping, by the data harvest engine, standardized format device attributes stored in the hidden layer nodes of the hidden data layer to one or more output data nodes of a data socialization layer for consumption by an application of the at least one data analysis engine.

In other features, the memory is configured to store a data hub including at least one blockchain, and storing the multiple data values sensed by the first monitor device includes storing the standardized format device attributes as one or more elements of the at least one blockchain. In other features, the memory is configured to store an uncultivated data harvester platform, and the instructions further include identifying, by the universal data curation platform, unused data values of the streaming health data that do not correspond to any of the multiple device profiles, suppling the identified unused data values to the uncultivated data harvester platform, and storing, by the uncultivated data harvester platform, the unused data values in a raw format.

In other features, the at least one data analysis engine includes a personalized micro-engine, and the instructions further include aggregating standardized format device attributes from the first monitor device and the second monitor device, determining, based on the aggregated attributes, an average efficacy of the first monitor device and the second monitor device, the average efficacy indicative of a measured health status of the first member and the second member, and comparing the average efficacy to a target device efficacy value to determine an outcome-based device efficacy of the first monitor device and the second monitor device.

In other features, the first monitor device is an Internet-of-Things (IoT) health monitor device associated with the first member and the second monitor device is an IoT health monitor device associated with the first member, the personalized micro-engine is a member-centric micro-engine, and the outcome-based device efficacy is a per-member value indicative of an efficacy across the first and second IoT health monitor devices for improving the measured health status of the first member. In other features, the first monitor device is an Internet-of-Things (IoT) health monitor device supplied by the first vendor and associated with the first member, and the second monitor device is an IoT health monitor device supplied by the first vendor and associated with the second member, the personalized micro-engine is a product-centric micro-engine, and the outcome-based device efficacy is a per-product value indicative of an efficacy across IoT health monitor devices supplied by the first vendor for improving the measured health status of the first member and the second member.

A computerized method of capturing monitor device data in a blockchain includes receiving a product identifier and product registration information for a monitor device supplied by a vendor, generating, by a blockchain secret device key ledger, a secret device key for the monitor device, and configuring the monitor device with the secret device key. The method includes receiving a member identifier and member registration information for a member associated with the monitor device, generating, by a blockchain secret member key ledger, a secret member key, linking the secret member key with the monitor device, and receiving, by a blockchain secret member-device association ledger, an associated pair of the secret device key with the secret member key to store the associated pair for further authentication and authorization by the blockchain secret member-device association ledger.

In other features, the blockchain secret device key ledger, the blockchain secret member key ledger, and the blockchain secret member-device association ledger, each comprise a ledger of a single blockchain. In other features, the method includes receiving, by a universal data curation platform, a data stream from the monitor device, the data stream including a device key and a member key, checking, by the universal data curation platform against the blockchain secret member-device association ledger, the received device key and member key to determine whether a valid association of the monitor device and the member exists, and in response to confirmation of the valid association of the monitor device and the member according to the received device key and member key and the blockchain secret member-device association ledger, standardizing and storing the data stream from the monitor device in a blockchain.

In other features, the blockchain is a first blockchain, and the method further includes, in response to confirmation of the valid association of the monitor device and the member according to the received device key and member key and the blockchain secret member-device association ledger, identifying non-classified data in the data stream, and supplying the identified non-classified data to a second blockchain of an uncultivated data harvester. In other features, the method includes supplying the standardized and stored data stream from the blockchain to one or more data analysis engines to determine a health status of the member.

A computerized method includes registering a first monitor device supplied by a first vendor, and associating the first monitor device with a first member, registering a second monitor device supplied by the first vendor or a second vendor, and associating the second monitor device with the first member or a second member, and receiving streaming health data from the first monitor device and the second monitor device, the received streaming health data including multiple data values sensed by the first monitor device and the second monitor device. The method includes identifying, by a universal data curation platform including multiple device profiles, a first one of multiple device profiles corresponding to the first monitor device, each device profile including multiple fields for storing received device attributes in a standardized format, and transforming and storing the multiple data values sensed by the first monitor device into standardized format device attributes of the identified device profile corresponding to the first monitor device. The method includes identifying, by the universal data curation platform, a second one of the multiple device profiles corresponding to the second monitor device, and transforming and storing the multiple data values sensed by the second monitor device into the standardized format device attributes of the identified device profile corresponding to the second monitor device, and supplying the stored standardized format device attributes to at least one data analysis engine to determine one or more health characteristics of at least one of the first member and the second member.

In other features, the standardized format device attributes include at least one of a device measurement value, a measurement type, a measurement timestamp, and a member identifier. In other features, the universal data curation platform comprises a hidden data layer including a data rationalization engine and multiple hidden layer nodes, receiving the streaming health data includes receiving multiple data packets from the first monitor device and the second monitor device at an external data layer, transforming and storing the multiple data values sensed by the first monitor device includes mapping data packets received from the first monitor device to the hidden layer nodes associated with the identified device profile corresponding to the first monitor device, and transforming and storing the multiple data values sensed by the second monitor device includes mapping data packets received from the second monitor device to the hidden layer nodes associated with the identified device profile corresponding to the second monitor device.

In other features, the method includes identifying, by the data rationalization engine, noise values in the streaming health data, and inhibiting storing of the noise values in the multiple hidden layer nodes of the hidden data layer. In other features, the hidden data layer of the universal data curation platform includes a data harvest engine, and supplying the stored standardized format device attributes includes mapping, by the data harvest engine, standardized format device attributes stored in the hidden layer nodes of the hidden data layer to one or more output data nodes of a data socialization layer for consumption by an application of the at least one data analysis engine.

A computerized method of automated device efficacy determination for multiple monitor devices includes receiving streaming data from multiple monitor devices, the received streaming data including multiple health data values sensed by the multiple monitor devices and indicative of health status of one or more members, identifying first health data values from a first target one of the multiple monitor devices, and identifying second health data values from a second target one of the multiple monitor devices. The method includes determining, by a personalized micro-engine, a first measured health status value of a first one of the members according to the identified first health data values, and determining, by the personalized micro-engine, a second measured health status value of the first member or a measured health status value of a second member according to the identified second health data values. The method includes aggregating, by the personalized micro-engine, the determined first measured health status value of the first member with the determined second measured health status value of the first member or the measured health status value of the second member, and comparing the aggregated measured health status values to a target device efficacy threshold to determine an outcome-based device efficacy of the first and second target monitor devices.

In other features, the first target monitor device is an Internet-of-Things (IoT) health monitor device associated with the first member and the second target monitor device is an IoT health monitor device associated with the first member, the personalized micro-engine is a member-centric micro-engine, and the outcome-based device efficacy is a per-member value indicative of the efficacy across the first and second target IoT health monitor devices for improving the measured health status of the first member.

In other features, identifying the first and second health data values includes identifying a member identifier corresponding to the first member and scanning the received streaming data for data values including the member identifier, and the method includes routing the data values including the member identifier to the personalized micro-engine. In other features, the personalized micro-engine includes multiple parallel processing nodes for processing data values corresponding to the first and second IoT health monitor devices in parallel, and routing the data values includes routing received data values from the first IoT health monitor device to a first one of the multiple parallel processing nodes and routing received data values from the second IoT health monitor device to a second one of the multiple parallel processing nodes.

In other features, the multiple parallel processing nodes are deployed in a Docker container of a Kubernetes platform. In other features, the first target monitor device is an Internet-of-Things (IoT) health monitor device supplied by a vendor and associated with the first member and the second target monitor device is an IoT health monitor device supplied by the vendor and associated with the second member, the personalized micro-engine is a product-centric micro-engine, and the outcome-based device efficacy is a per-product value indicative of the efficacy across the first and second target IoT health monitor devices supplied by the vendor for improving the measured health statuses of the first and second members.

In other features, identifying the first and second health data values includes identifying a product identifier corresponding to the first and second target IoT health monitor devices supplied by the vendor and scanning the received streaming data for data values including the product identifier, and the method includes routing the data values including the product identifier to the personalized micro-engine. In other features, the personalized micro-engine includes multiple parallel processing nodes for processing data values corresponding to the first and second IoT health monitor devices in parallel, and routing the data values includes routing received data values from the first IoT device to a first one of the multiple parallel processing nodes and routing received data values from the second IoT health monitor device to a second one of the multiple parallel processing nodes.

In other features, the multiple parallel processing nodes are deployed in a Docker container of a Kubernetes platform. In other features, receiving the streaming data from multiple IoT health monitor devices includes standardizing, by a universal data curation platform, the received multiple health data values of the received streaming data into a standardized attribute format according to one or more device profiles associated with the first and second target IoT health monitor devices, storing the standardized attributes in a blockchain, and supplying the standardized attributes to the personalized micro-engine.

In other features, the method includes determining a reimbursement rate for a vendor of at least one of the first and second target monitor devices according to the outcome-based device efficacy of the first and second monitor devices, and displaying at least one of the determined reimbursement rate and the outcome-based device efficacy of the first and second target monitor devices on a digital portal.

A computer system includes memory configured to store computer-executable instructions and a personalized micro-engine, and at least one processor configured to execute the instructions. The instructions include receiving streaming data from multiple monitor devices, the received streaming data including multiple health data values sensed by the multiple monitor devices and indicative of health status of one or more members, identifying first health data values from a first target one of the multiple monitor devices, identifying second health data values from a second target one of the multiple monitor devices, and determining, by the personalized micro-engine, a first measured health status value of a first one of the members according to the identified first health data values. The instructions include determining, by the personalized micro-engine, a second measured health status value of the first member or a measured health status value of a second member according to the identified second health data values, aggregating, by the personalized micro-engine, the determined first measured health status value of the first member with the determined second measured health status value of the first member or the measured health status value of the second member, and comparing the aggregated measured health status values to a target device efficacy threshold to determine an outcome-based device efficacy of the first and second target monitor devices.

In other features, the first target monitor device is an Internet-of-Things (IoT) health monitor device associated with the first member and the second target monitor device is an IoT health monitor device associated with the first member, the personalized micro-engine is a member-centric micro-engine, and the outcome-based device efficacy is a per-member value indicative of the efficacy across the first and second target IoT health monitor devices for improving the measured health status of the first member.

In other features, identifying the first and second health data values includes identifying a member identifier corresponding to the first member and scanning the received streaming data for data values including the member identifier, and the instructions further include routing the data values including the member identifier to the personalized micro-engine. In other features, the personalized micro-engine includes multiple parallel processing nodes for processing data values corresponding to the first and second IoT health monitor devices in parallel, and routing the data values includes routing received data values from the first IoT health monitor device to a first one of the multiple parallel processing nodes and routing received data values from the second IoT health monitor device to a second one of the multiple parallel processing nodes.

In other features, the multiple parallel processing nodes are deployed in a Docker container of a Kubernetes platform. In other features, the first target monitor device is an Internet-of-Things (IoT) health monitor device supplied by a vendor and associated with the first member and the second target monitor device is an IoT health monitor device supplied by the vendor and associated with the second member, the personalized micro-engine is a product-centric micro-engine, and the outcome-based device efficacy is a per-product value indicative of the efficacy across the first and second target IoT health monitor devices supplied by the vendor for improving the measured health statuses of the first and second members.

In other features, identifying the first and second health data values includes identifying a product identifier corresponding to the first and second target IoT health monitor devices supplied by the vendor and scanning the received streaming data for data values including the product identifier, and the instructions further include routing the data values including the product identifier to the personalized micro-engine. In other features, the personalized micro-engine includes multiple parallel processing nodes for processing data values corresponding to the first and second IoT health monitor devices in parallel, and routing the data values includes routing received data values from the first IoT device to a first one of the multiple parallel processing nodes and routing received data values from the second IoT health monitor device to a second one of the multiple parallel processing nodes. In other features, the multiple parallel processing nodes are deployed in a Docker container of a Kubernetes platform.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

FIGS. 6A and 6B together form a message sequence chart showing example interactions between components of the system of FIG. 4 during client registration and streaming of data from health monitoring devices.

FIGS. 8A and 8B together form a message sequence chart showing example interactions between components of the system of FIG. 4 during registration of a product and a member to a data hub.

In the drawings, reference numbers may be reused to identify similar and/or identical elements.

DETAILED DESCRIPTION

High-Volume Pharmacy

Figure 1:
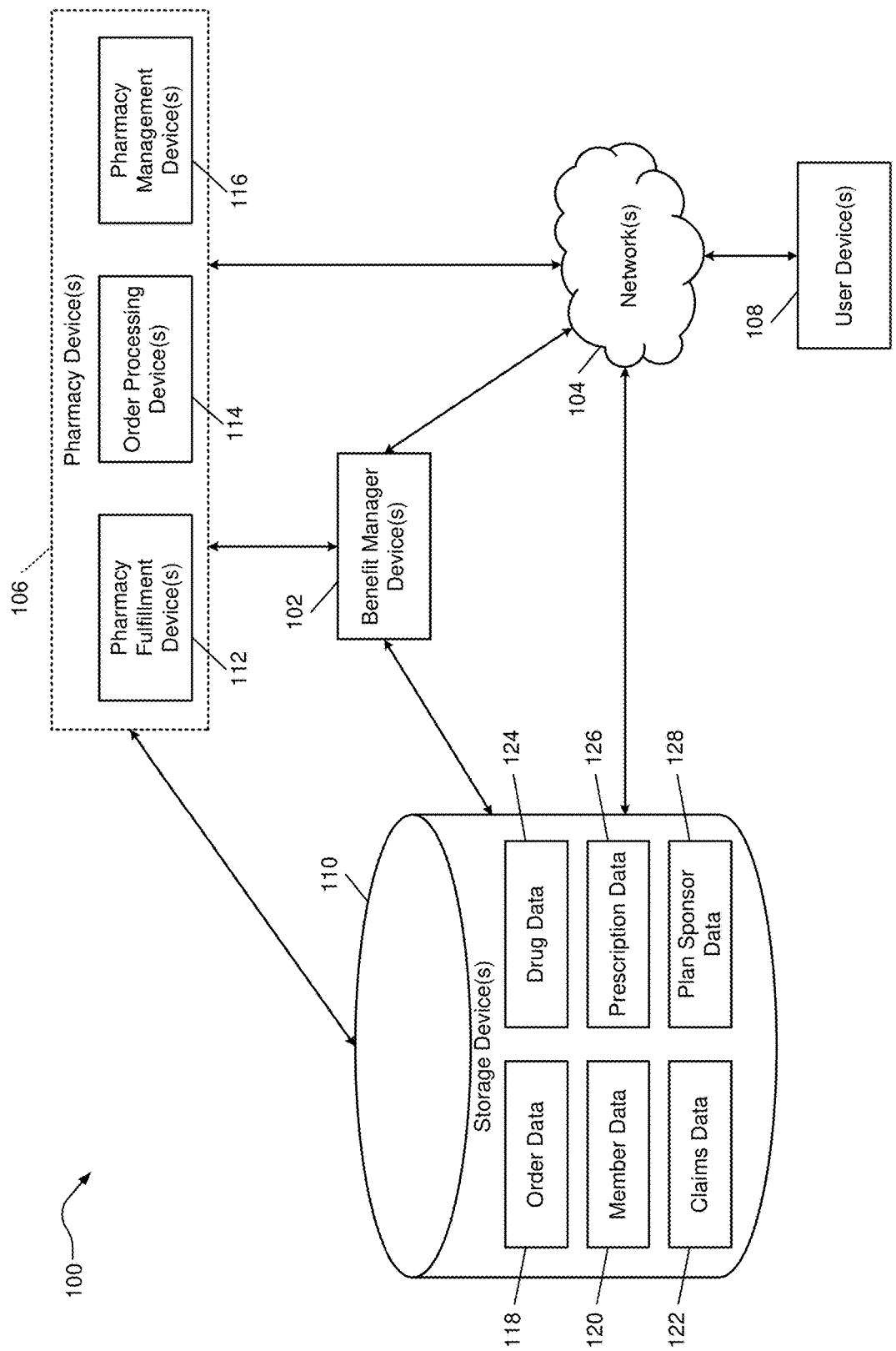
FIG. 1 is a functional block diagram of an example system including a high-volume pharmacy.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfillment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
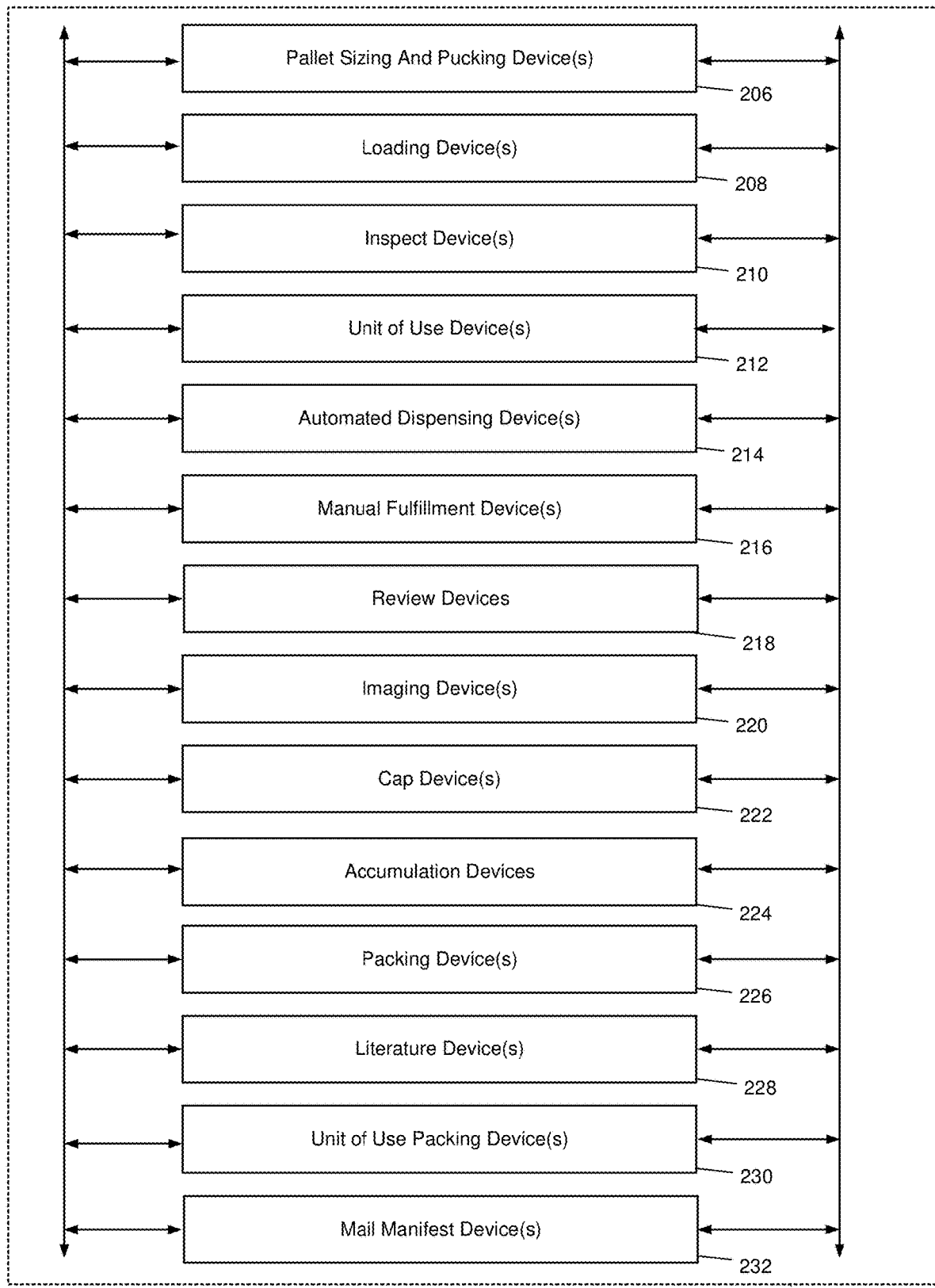
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
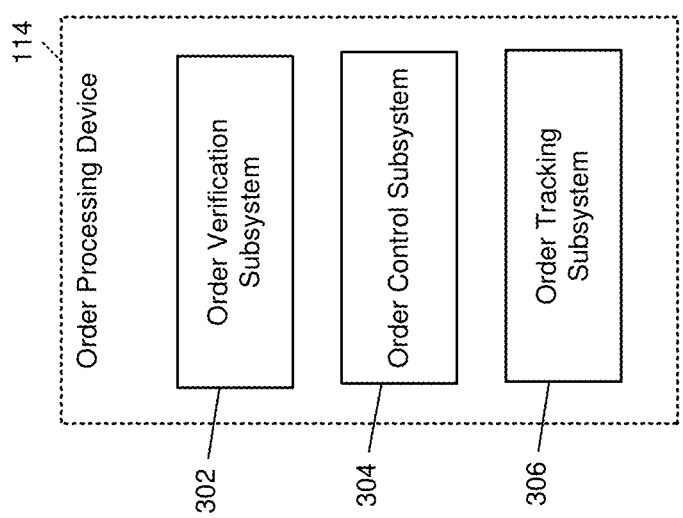
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Health Insights System

In various implementations, a health insights system facilitates universal data curation from multiple monitor devices (e.g., Internet-of-things (IoT) health monitor devices), provided by different vendors. For example, the system may register multiple smart watches, fitness trackers, smartphones, blood glucose monitors, blood pressure monitors, etc., from different vendors, which may be registered to different members that belong to different client organizations, and all of the devices may stream health data for the different members to a universal data curation platform. In addition, one or more vendor cloud data processing and storage systems may stream health data for multiple members to the universal data curation platform.

The incoming data from the various devices, disparate vendors, different cloud systems, etc., may include raw and noisy data streams, incomplete data, etc. The universal data curation platform receives the data streams and provides transformation and standardization of the data into a universal format for use by downstream applications, processing engines, etc. In various implementations, received data that is interpretable by existing applications may be forwarded downstream, while unknown or unrecognizable data is stored in an uncultivated data harvester for later use (e.g., the uncultivated data may include noise, may not fit in any universal or standardized data format, etc.).

The standardized data may be stored in a data hub, in order to create an immutable, time-stamped, secure and unalterable ledger for storing incoming data from the IoT devices and vendor cloud systems in a digital format. The data hub may provide role-based access control to ensure correct authentication and authorization protocols are followed before providing access to any data stored on the platform.

For example, the data hub may follow a multi-step registration process where a device is first registered and then configured with a secret device key, and separately a member is registered and the member is provided with a secret member key. The device is linked to the secret member key, and the associated secret device key and secret member key are provided to an association ledger of the secret device and member keys.

Subsequently, when health data (e.g., clinical data, etc.) is streamed from the device, the blockchain may check for a valid device and member association before returning an authorization to permit the streaming data to be added to the blockchain. In contrast to merely registering a device individually, or registering a member individually, the multi-step registration process may help ensure that a device is properly associated with and is currently being used by the correct member, to facilitate accurate storage and access to sensitive health data.

In various implementations, one or more personalized micro-engines may monitor efficacy of devices on a per-member basis, a per-product basis, etc. For example, if a vendor advertises that their smart blood pressure monitor will lead to a reduction of a user's blood pressure by 10% over a three month period, a personalized micro-engine may monitor health data from multiple different members that are each using the specific vendor's smart blood pressure monitor, and determine the actual reduction in blood pressure over the three month time period across the multiple users.

The efficacies of the vendor device for multiple members may be aggregated by the personalized micro-engine to determine an overall outcome for the vendor device. The overall outcome may be supplied to a client organization that includes the multiple members, in order for the client organization to determine whether to increase use of the vendor device among its members, stop use of the vendor device, etc.

For example, if the overall outcome is only a 1% reduction in blood pressure over three months (much less than the 10% advertised by the vendor), the client organization may decide whether the results are worth the costs of the vendor device. In various implementations, the device efficacy may be used to determine payment to the vendor, where the client organization may provide higher payments for better results, lower payments for worse results, etc. This may incentivize the vendor to provide effective devices, continually improve their devices, provide more honest advertisement about estimated device efficacy, etc. This may also save money for the client organization for devices that are not effective, help to ensure that the client organization is spending money more efficiently on vendor devices that provide greater benefits to its members, etc.

Figure 4:
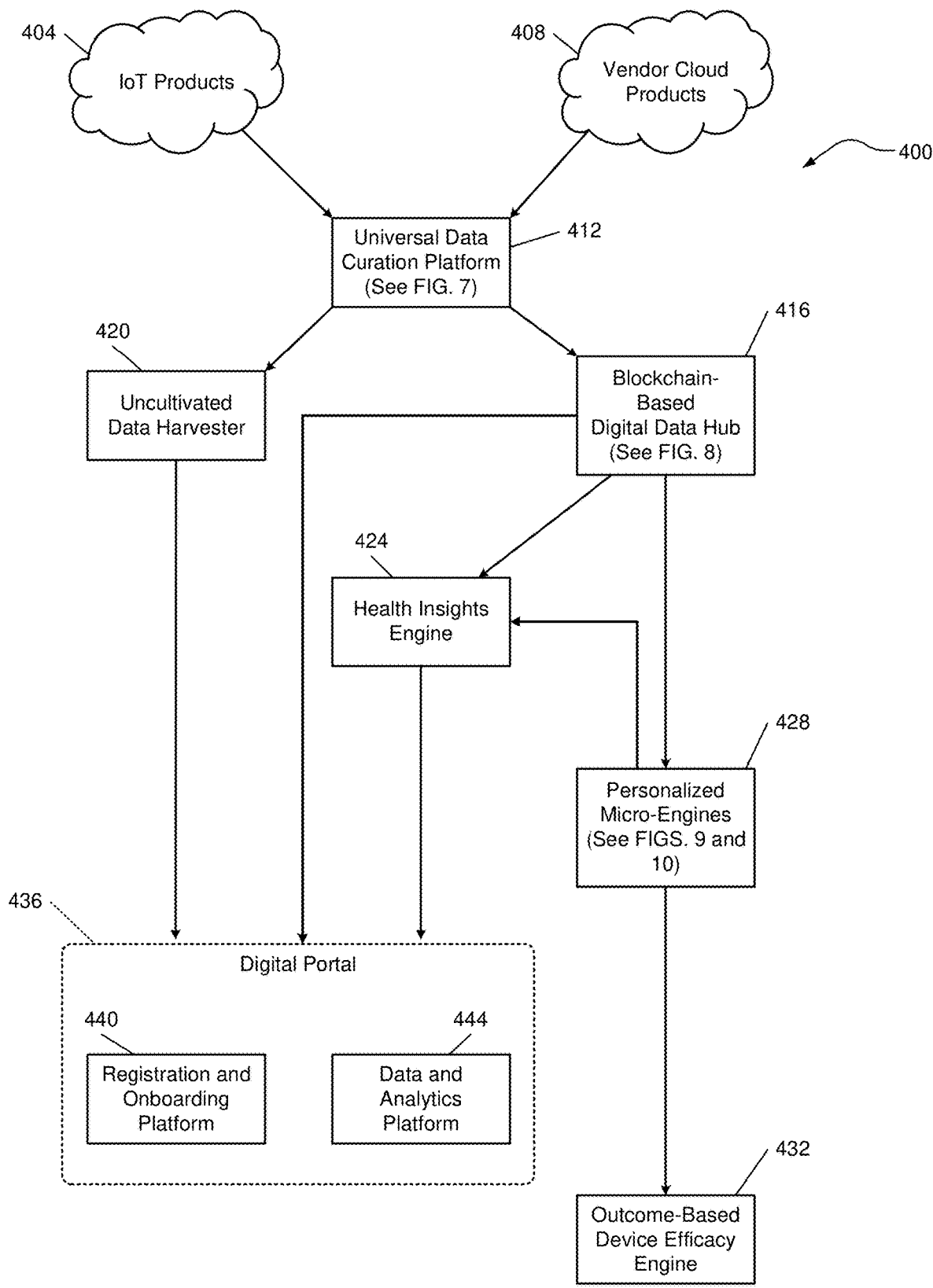
FIG. 4 is a functional block diagram of an example automated device efficacy determination system for health monitoring devices.

FIG. 4 is a block diagram of an example implementation of a system 400 for automated device efficacy determination of health monitor devices. Components of the system 400 may be located in one or more storage devices, such as the storage device 110 of FIG. 1. The system 400 is generally described as being deployed in a computer network system, and components of the system 400 may communicate with one another via one or more networks, such as the network 104 of FIG. 1. Components of the system 400 may be deployed on one or more devices including a desktop computer, a laptop computer, a tablet, a smartphone, a health monitor device, etc.

As shown in FIG. 4, the system 400 includes a universal data curation platform 412 that receives streaming data from monitor device products 404 (such as IoT health monitor devices), and/or vendor cloud products 408. The universal data curation platform 412 standardizes the raw and noisy streaming health data received from the IoT health monitor products 404 and/or the vendor cloud products, and distributes data to a blockchain-based digital data hub 416 and/or a blockchain-based uncultivated data harvester 420. The data hub 416 provides data to personalized micro-engines 428, a health insights engine 424, and/or a digital portal 436. The digital portal 436 includes a registration and onboarding platform 440 and a data and analytics platform 444. The personalized micro-engines supply data to the outcome-based device efficacy engine.

The universal data curation platform 412, the data hub 416, the data harvester 420, the health insights engine 424, the personalized micro-engines 428, the digital portal 436 and the outcome-based device efficacy engine 432 may be located in different physical memories (e.g., within the storage device 110, etc.), such as different random access memory (RAM), read-only memory (ROM), a non-volatile hard disk or flash memory, etc. In some implementations, one or more of the universal data curation platform 412, the data hub 416, the data harvester 420, the health insights engine 424, the personalized micro-engines 428, the digital portal 436 and the outcome-based device efficacy engine 432 may be located in the same memory (e.g., in different address ranges of the same memory, etc.).

The universal data curation platform 412 may receive data from the IoT products 404 and/or the vendor cloud products 408 via any suitable network, such as the network 104 of FIG. 1. Example networks for transmitting streaming health data from the IoT products 404 and/or the vendor cloud products 408 to the universal data curation platform 412 may include a wireless network, a local area network (LAN), the Internet, a cellular network, etc. Similarly, the universal data curation platform 412, the data hub 416, the data harvester 420, the health insights engine 424, the personalized micro-engines 428, the digital portal 436 and the outcome-based device efficacy engine 432 may communicate with one another via any suitable network when any of the components are located on different devices, in different storage memories, etc.

A system administrator, a member, a vendor, a client organization, etc., may interact with components of the system 400 to implement the automated device efficacy determination for streaming health monitor devices, via a user device, such as the user device 106 of FIG. 1. For example, a vendor may access the system 400 to register a streaming health monitor device, a member may access the system 400 to provide member information for registration, a client organization may access the system 400 to monitor efficacy of devices used in a program of the client organization, etc. The user device may include any suitable device for receiving input and supplying outputs to a user, such as a desktop computer, a laptop computer, a tablet, a smartphone, etc. The user device may access the storage devices of the system 400 directly, or may access storage devices through one or more networks. Example networks may include a wireless network, a local area network (LAN), the Internet, a cellular network, etc.

The IoT products 404 may include any suitable devices providing health monitoring data the member to the universal data curation platform 412. For example the IoT products 404 may include smart watches, fitness trackers, smart phones, blood pressure monitors, glucose monitors, etc. Each product 404 may provide the stream of data to the universal data curation platform 412, such as a continuous stream of clinical data of the member carries the product 404, wears the product 404, uses the product 404, etc. As described further herein, each product 404 may be registered to the system 400 and associated with the specified member at the time of registration.

The vendor cloud products 408 may include any suitable health data stream from the vendor cloud system. For example, monitored health data from one or more devices of the member, medical records, etc., may be stored on a vendor cloud, and data from the vendor cloud may be streamed directly to the universal data curation platform 412. In various implementations data from the vendor cloud products 408 may be similar to data that would be streamed from IoT products 404, may be different than data that would be streamed from IoT products 404, etc. Vendor cloud products 408 are registered to the system 400 and associated with specified members at the time of registration.

The data stream to the universal data curation platform 412 may be raw data that contains noise, may be in different formats depending on different products 404 and/or 408, etc. For example, the data may be obtained from the products 404 or the vendor cloud products 408 via an open IoT level public domain, etc. The universal data curation platform 412 may transform the received data into a universal layout so that the data has a standardized format for use by downstream applications. For example universal data curation platform 412 may use a common global clinical data dictionary to format data as is received from the products 404 and 408, thereby presenting standard data layout for downstream applications to use even when the data comes from disparate IoT products 404 and vendor cloud products 408.

As shown in FIG. 4, the standardized data from the universal data curation platform 412 may be supplied to a data hub 416. The data hub 416 may receive known/structured/usable data from the universal data curation platform 412, and store the data in an immutable, timestamped, secure, and unalterable ledger to maintain the data in a digital format. As described further herein, the data hub 416 may provide role-based access control to ensure proper authentication and authorization protocols are followed before giving access to data stored in the data hub 416.

Separately, data that is not yet standardized, does not fit in a known universal format, etc., may be supplied from the universal data curation platform 412 to the data harvester 420. Data in the data harvester 420 may not have all noise removed, may include bugs or errors, or be incomplete, etc. This data is saved in the data harvester 420 (possibly in a blockchain-based format), for potential later use if additional features or further understanding of the unused data is later implemented in the system 400.

For example, if a product 404 supplies both weight information and body mass index (BMI) information to the universal data curation platform 412, but only the weight information is a currently used standardized format (e.g., downstream applications are only using weight information currently), the standardized weight information may be supplied to the data hub 416 while the BMI information is supplied to the data harvester 420. The data harvester 420 saves the BMI data stream from the product 404, and if at a later date the system 400 is updated so that one or more applications wishes to use the BMI information, the historical BMI data saved in the data harvester 420 can be used by the applications at that later date.

As shown in FIG. 4, the data hub 416 supplies data to the health insights engine 424. The health insights engine 424 may identify, determine, calculate, etc., different health trends and insights for the individual member health, based on the received streaming data from the product(s) 404 and/or 408. For example, the health insights engine 424 may determine improving or declining trends in different health aspects of the member based on the received streaming data over time, the health insights engine 424 may generate new intervention opportunities based on insights into the member health from the received streaming health data, etc.

In various implementations, the health insights engine 424 may determine whether a member's blood pressure is increasing or decreasing over time, whether a member's weight is increasing or decreasing over time, changes in activity levels over time, etc. These changes may be used to determine whether an intervention should occur to assist in improving the health status of the member (e.g., when the member health data indicates the member health status is declining, etc.).

Data from the health insights engine 424, the data hub 416, and/or the data harvester 420, may be supplied to the digital portal 436. The digital portal 436 may allow parties to view the results of analysis by the system 400 for a variety of different factors. For example, vendors may analyze data to determine how their products are performing, financial remittance and billing may be determined based on the performance of their products, etc.

Members may access the digital portal 436 to monitor their own health status based on the streaming data from the IoT products 404 and/or vendor cloud products 408. Client organizations may access the digital portal 436 to determine the efficacy of devices used in any client organization sponsored programs, may use the determined efficacies to identify remittance and billing rates for different vendors based on the effectiveness of different products, etc.

The digital portal 436 may include a registration and onboarding platform 440 that allows the IoT products 404 and/or vendor cloud products 408 to be registered to the system 400. The registration and onboarding platform 440 may also allow members to register, client organizations to register, etc. The data and analytics platform 444 of the digital portal 436 may provide different insights about the effectiveness of the IoT products 404 and/or vendor cloud products 408, may provide analytics about health of members based on streaming data for the IoT products 404 and/or vendor cloud products 408, may provide data about the effectiveness of different program options for client organization utilizing one or more products 404 and/or vendor cloud products 408, etc. The data and analytics platform 444 may provide similar analysis as the health insights engine 424, may display data output from the personalized micro-engines 428 or the outcome-based device efficacy engine 432, etc.

For example, and as described further below, the personalized micro-engines 428 may analyze the standardized streaming data on a per-member level to evaluate the effectiveness of different products 404 and/or vendor cloud products 408 for a single member, may analyze the standardized streaming data on a per-product level to determine effectiveness of a single product 404 and/or vendor cloud products 408 across multiple members, etc. Output from the personalized micro-engines 428 may be supplied to the outcome-based device efficacy engine 432, which aggregates the data to determine effectiveness of multiple products for a single member, or multiple members using a single product, and outputs a result of the aggregate effectiveness for analysis by the vendor, by a client organization, etc.

For example, a member using multiple products 404 and/or vendor cloud products 408 may identify which are the most effective in order to eliminate the least effective options to save money, to focus on using the most effective products 404 and/or vendor cloud products 408 more often, etc. Client organizations may analyze results of the outcome-based device efficacy engine 432 to determine how much money to pay vendors (e.g. based on whether or not the efficacy of the vendor device matched a target value advertised by the vendor, etc.). The client organization can determine whether to continue using the product in one of their programs, to discontinue the product from their program, to increase use of the product if it is shown to have a high efficacy for members of the client organization's program, etc.

Vendors may view results of the outcome-based device efficacy engine 432 to check whether their specific products 404 and/or 408 are providing the desired efficacy in the field, as used by actual members. Vendors can determine which products need to be improved, which products may be discontinued or are not cost effective, etc. Vendors may adjust advertising to future potential client organizations and/or members based on historical results from the outcome-based device efficacy engine 432, may negotiate reimbursement for billing rates based on the results from the outcome-based device efficacy engine 432, etc.

As an example, the vendor may advertise that use of the vendor's fitness tracker product will lead to a 20% increase in the number of steps per day of members who use the device over a six-month period. The personalized micro-engine 428 may aggregate data for multiple members that each use specified fitness tracker product, and after six months compare the resulting step count improvement to the target step count improvement of 20%, to determine outcome-based device efficacy of the fitness tracker product.

A resulting improvement of greater than the target value of 20% may indicate that the vendor fitness tracker product is highly effective and the client organization should continue supplying the fitness tracker product to its members in the program, may indicate that the vendor should receive full billing payment or even a bonus from the client organization and/or members, etc. In contrast, a resulting improvement value of less than the target value of 20%, such as only a 5% step count improvement after six months, may indicate that the vendor should receive less than full billing payment because the product was not as effective as advertised, may indicate that the client organization should stop supplying the product to its members, etc.

Figure 5:
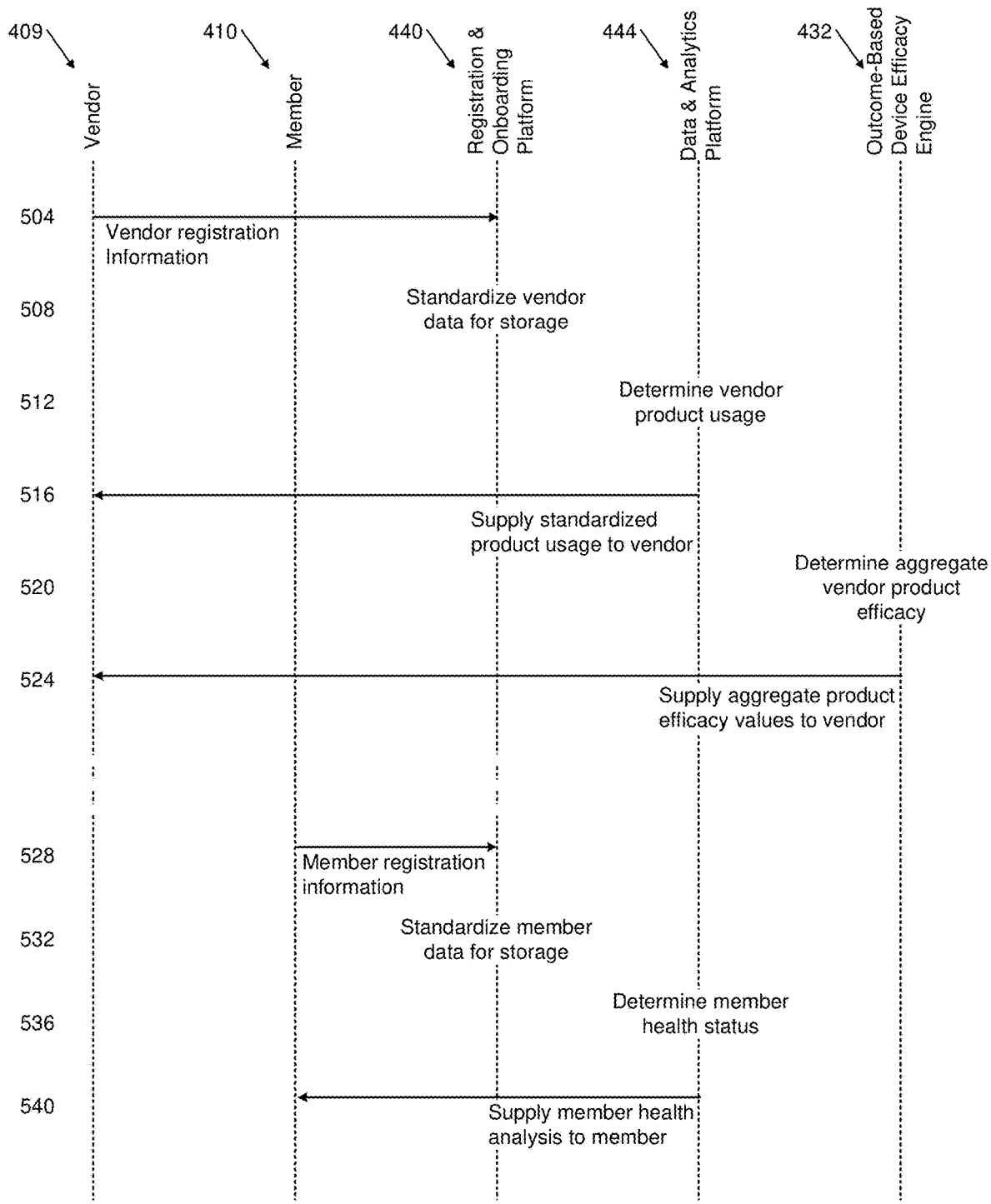
FIG. 5 is a message sequence chart showing example interactions between components of the automated device efficacy determination system of FIG. 4.

FIG. 5 is a message sequence chart illustrating example interactions between a vendor 409, a member 410, a registration and onboarding platform 440, a data and analytics platform 444, and an outcome-based device efficacy engine 432, during registration of a new vendor and a new member. At line 504, the vendor 409 supplies vendor registration information to the registration and onboarding platform 440. For example, the vendor may supply one or more data attributes such as a vendor ID, name, contact person, and address, effective start and end dates of the vendors association with the system 400, etc. In various implementations, the vendor may supply financial information such as payable amounts for its products, billing payment to the vendor, billing quantity, pricing formulas for products of the vendor, etc.

At line 508, the registration and onboarding platform 440 standardizes the received vendor data for storage, such as for storing in the universal data curation platform 412. For example, the data from the vendor may be transformed into a universal data layout that includes a standardized format even for disparate types of vendors. Table 1 below illustrates an example template for storing standardized attributes of vendor information, such as in the universal data curation platform 412. When the vendor registration information is received by the registration and onboarding platform 440, the platform may determine which fields/attributes the vendor information corresponds to, and transform the vendor information into the appropriate field/attributes.

TABLE 1

| Vendor Attributes | Member Attributes |
| --- | --- |
| Vendor ID | Enrollment ID (Activation Code) |
| Name | Effective Start and End Dates |
| Contact Person | Member ID |
| Address | |
| Effective Start and End Dates | |
| Payable Amounts | |
| Billing Periods | |
| Billing Quantities | |
| Pricing Formulas | |
| User Count Per Product | |
| Product Count | |

At line 512, the data and analytics platform 444 determines usage of the vendor products. For example, the data and analytics platform 444 may determine any suitable data about how the products of the vendor are used by the members. Table 1 illustrates example values of a total product count of the vendor (e.g., the total number of products used by members in programs of the client organization program, etc.), and a user count per product (e.g., a breakdown of how many members are using each of different products of the vendor).

Although Table 1 lists specific attributes that may be stored for the vendor, in various implementations other suitable attributes of the vendor may be standardized, such as a number of products sold, a number of member registrations, a number of renewed subscriptions, a percentage of members that are actively engaged in using the product, a frequency of taking measurements with the product, etc. At line 516, standardized product usage data is supplied from the data and analytics platform 444 to the vendor 409.

At line 520, the outcome-based device efficacy engine 432 determines an aggregate efficacy for a vendor product. For example, the outcome-based device efficacy engine 432 may analyze outputs of the personalized micro-engine 428 to determine efficacy of a specific vendor product 404 across multiple members, and the resulting outcome-based device efficacy values are supplied to the vendor at line 524. These values may be used to determine remittance to the vendor, determine billing amounts or other financial information for the vendor according to the success of the device, etc.

Member registration information is supplied from the member 410 to the registration and onboarding platform 440 at line 528. For example, the member 410 may provide registration information such as an enrollment ID or activation code for the member to use the product from the vendor 409 in order to join a program of a client organization, etc. The member 410 may supply effective start and end dates of the member's registration to use the product or be part of the client organization's program, etc. The member 410 may supply a specific member ID, which may be different than the enrollment ID or activation code. Example values are illustrated in Table 1 above, although in various implementations other suitable attributes may be stored for the member 410. At line 532, the registration and onboarding platform 440 standardizes the member data for storage, such as in the universal data curation platform 412.

At line 536, the data and analytics platform 444 determines health status of the member based on data received from the product 404 associated with the member 410. For example, the data and analytics platform 444 may determine changes in the member's health such as changes in weight, changes in blood pressure, changes in glucose, changes in user activity levels, etc. The results of this analysis are supplied from the data and analytics platform 444 to the member 410 at line 540.

Figure 6A:
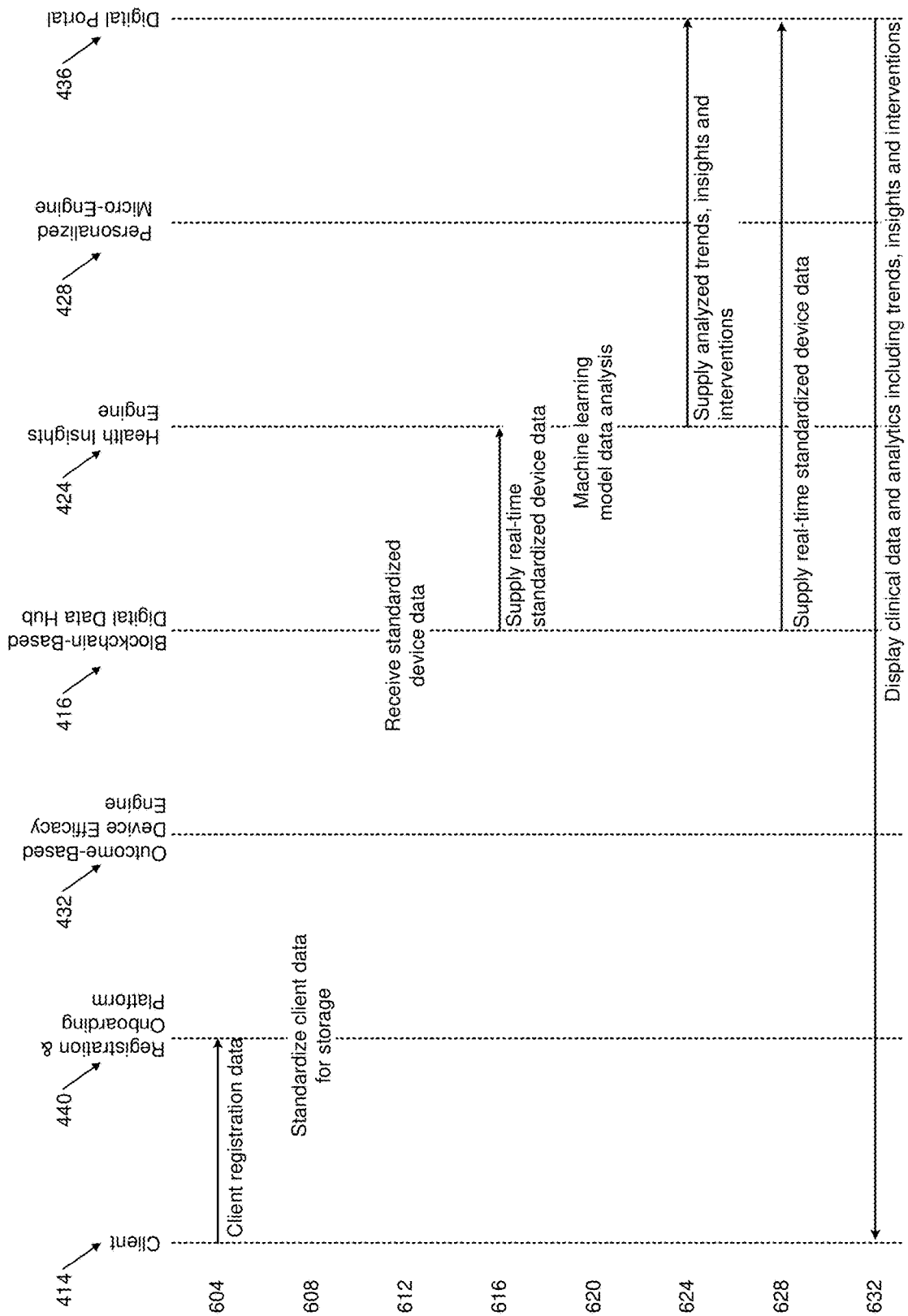

FIGS. 6A and 6B are a message sequence chart illustrating example interactions between a client 414, a registration and onboarding platform 440, an outcome-based device efficacy engine, the data hub 416, a health insights engine 424, a personalized micro-engine 428 and a digital portal 436, during operation of the system 400.

At line 604, the client 414 supplies registration data to the registration and onboarding platform 440. The client 414 may be any organization that provides a program for its members, such as a pharmacy, a hospital, a healthcare provider, a corporation, etc. The registration and onboarding platform 440 may standardize the data for storage at line 608, such as for storage in the universal data curation platform 412. Table 2 below lists example attributes of the client 414 that may be standardized for storage.

TABLE 2

| Client Attributes | Product Attributes |
|---|---|
| Client ID | Product ID |
| Effective Start and End Dates | Vendor ID |
| IDs of Subscribed Products/Services | Product Name |
| Measurement Values | Product Type |
| Measurement Types | Support Contact |
| Units | Cost Structure |
| Timestamp | Version |
| Member ID | Effective Start and End Dates |
| Receivable Amount | Measurement Values |
| Billing Period | Measurement Types |
| Billing Quantity | Units |
| Pricing Formula | Timestamp |
| Member-Level Analytical Data | Member ID |
| Masked Analytical Data | |

As shown in Table 2 above, the example client attributes may include an ID of the client, effective start and end dates of the client program, IDs of subscribed products or services that are part of the client program, measurement values and measurement types for the products and services of the client program (e.g., measurements included in the streaming data from the products/services, etc.), units for the measurements, timestamps of the measurements, member IDs associated with the product/services, etc.

The client attributes may include financial information such as receivable amounts, billing periods, billing quantities, pricing formulas for the products/services, etc. The universal data curation platform 412 may store analytical client information, such as member-level analytical data for carve-in subscribers, masked analytical data for carve-out subscribers, etc. In various implementations, other suitable attributes may be stored for the client 414.

As mentioned above, data may be stored for the products/services that are used by the system 400, such as products/services that are subscribed to by members as part of a program of the client 414. The products may have their own information/attributes that are standardized and stored, which may be provided at the time of registration by the vendor 409, at the time of registration by the client 414, etc. Example product attributes are illustrated in Table 2 above, and may include an ID of the product, an ID of the vendor providing the product, the name of the product, a type of product, the support contact for assistance regarding the product, a cost structure for the product (e.g., device fees, usage fees, service fees, etc.), a version of the product, effective start and end dates for using the product etc.

In various implementations, the universal data curation platform 412 may include multiple device profiles that each have their own corresponding universal format for storing standardized data and attributes for the product. When a product is registered by a vendor or a client (or a member), the universal data curation platform 412 may search to identify a profile that matches the type and/or ID of the registered product. The device profile may identify the type of device, the type of data that is expected from the device, a universal format of how the received data will be transformed and stored, etc. If the existing profile matches the registered product, the registered product may be assigned to that type of profile for storing and transforming received data from the registered product. Alternatively, a new profile may need to be created for the device in order to create a standardized universal format for data received from the device.

Therefore, as opposed to a system that only handles one type of streaming data from one type of device, the universal data curation platform 412 allows multiple disparate devices to all stream data to the universal data curation platform 412, where the data from the different devices will be stored in the universal standardized format for use by downstream applications.

Referring to Table 2 again, streaming product data that may be stored in the universal attribute format may include measurement values, measurement types (e.g., weight, pressure, steps, etc.), units (e.g., pounds, millibars, total count per day, etc.), a timestamp of the received values, a member ID associated with the received streaming value the product, etc. For example, for a heart rate monitoring device, the measurement values may be 65, the measurement type is a heart rate or pulse, the unit is frequency in hertz, the timestamp is the time that the current measurement was taken, the member ID identifies the member wearing the heart rate monitor, etc.

At line 612, the data hub 416 receives standardized device data (e.g., from the universal data curation platform 412, etc.). At line 616, the data hub 416 supplies real-time standardized device data to the health insights engine 424. The health insights engine 424 then analyzes the standardized data at line 620, and supplies analyzed trends, insights and/or interventions to the digital portal at line 624.

For example, the health insights engine 424 may implement one or more machine learning models (such as a random forest model, etc.), in order to determine health status information about a member. In various implementations, the health insights engine 424 may determine a normal baseline value for a member (e.g., a baseline value for streaming data from a health monitor device product 404, etc.), and then compare currently received streaming data to the baseline to determine whether any health issues have occurred. The health insights engine 424 may use machine learning models to identify early intervention opportunities that could improve the health status of the member.

The data hub 416 also supplies the standardized device data to the digital portal 436 at line 628, which allows the digital portal 436 to display standardized data itself as desired, along with the analyzed trends, insights and interventions from the health insights engine 424. For example, at line 632, the digital portal 436 displays the clinical data to the client 414 along with the analytical insights, trends and interventions.

At line 636, the data hub 416 supplies real-time standardized device data to the personalized micro-engine 428. The personalized micro-engine 428 then determines the per-member or per-product device efficacy at line 640. For example, the personalized micro-engine 428 may aggregate all data across multiple products of a single member, may aggregate all data from a single type of device that is used by multiple members, etc. The personalized micro-engine 428 then supplies determined per-member and/or per-product device efficacy to the outcome-based device efficacy engine 432 at line 644.

Data Curation Platform

Figure 7:
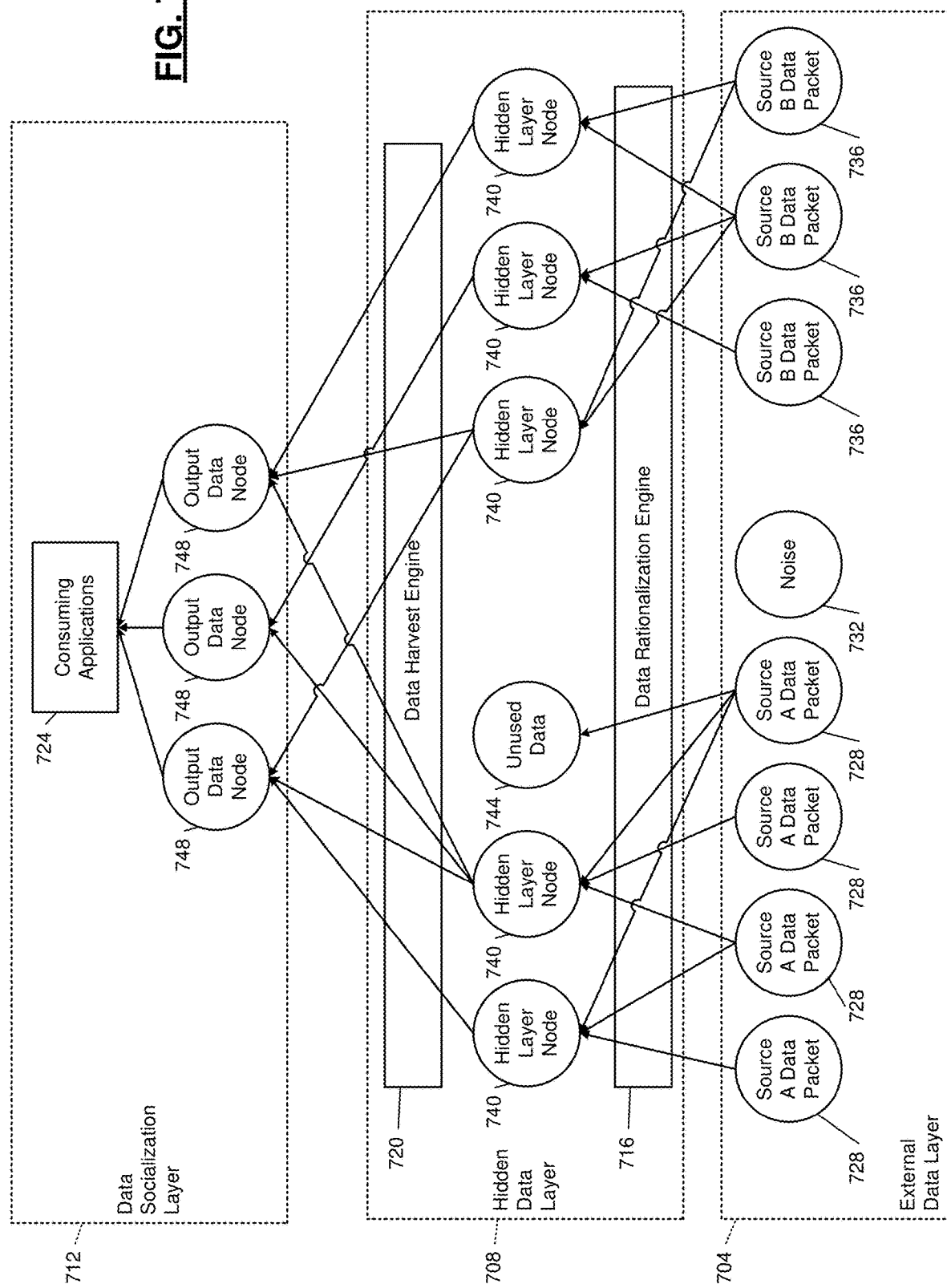
FIG. 7 is a functional block diagram of an example universal data curation platform.

FIG. 7 is an example flow diagram for the universal data curation platform 412. As shown in FIG. 7, an external data layer 704 receives multiple data packets 728 from source A (e.g. a first health monitor device product 404), and the external data layer 704 receives multiple data packets 736 from a source B (e.g., a second health monitor device product 404). The external data layer 704 also receives noise 732. In this example, the data packets may represent streaming data from health monitor devices that are received by the universal data curation platform 412.

A hidden data layer 708 includes a data rationalization engine 716. The data rationalization engine receives the data packets 728 and 736 streamed from the source A device and the source B device. Noise 732 in the streaming data may be rejected by the data rationalization engine 716.

The data rationalization engine 716 attempts to match the incoming data to a stored data model or universal format profile, which may be stored in the hidden layer nodes 740. For example, the data rationalization engine 716 may include one or more algorithms, trained models, programs, etc., that determine which hidden layer nodes 740 should store data packets from source A and source B. The hidden layer nodes 740 may be optimized to record and store the incoming data, and may include a mapping of the incoming data to specified fields in the hidden layer nodes 740.

The hidden data layer 708 also includes a node 744 for unused data. The data rationalization engine 716 may use a screen to move data that is not currently usable to the unused data node 744. The data in the unused data node 744 may be stored in a raw format, as a binary object, etc.

The hidden data layer 708 also includes a data harvest engine 720. The data harvest engine 720 formats classless data be used or consumed by downstream applications. For example, the data harvest engine 720 may supply data from hidden layer nodes 740 to output data nodes 748 of the socialization layer 712. The output data nodes 748 supply the appropriate data to consuming applications 724, such that the consuming applications 724 can receive standardized data originating in the data packets 728 and 736 of multiple IoT products.

Data Hub

FIGS. 8A and 8B are a message sequence chart illustrating example interactions between an IoT product 404, a member 410, a vendor 409, a registration and onboarding platform 440, a universal data curation platform 412, a blockchain secret device key ledger 416-1, a blockchain secret member key ledger 416-2, a blockchain secret member-device association ledger 416-3, the data hub 416, and the data harvester 420, during registration of the product 404 and member 410 to supply data to the data hub 416.

At line 804, a vendor 409 supplies product information to the registration and onboarding platform 440. The registration and onboarding platform 440 then supplies product ID and device information to the blockchain secret device key ledger 416-1, at line 808. At line 812, the blockchain secret device key ledger 416-1 generates and provides a secret device key to the vendor 409. The vendor 409 then configures the specific device with its assigned secret device key at line 816.

At line 820, a member 410 supplies member information to the registration and onboarding platform 440. At line 824, the registration and onboarding platform 440 then supplies the member information to the blockchain secret member key ledger 416-2. At line 828, the blockchain secret member key ledger 416-2 provides the generated secret member key to the member 410 based on the received member information.

The member 410 links the secret member key to the product 404 at line 832. The product 404 than provides the associated secret device key and secret member key to the blockchain secret member-device association ledger 416-3 at line 836. The blockchain secret device key ledger 416-1, the blockchain secret member key ledger 416-2, and the blockchain secret member-device association ledger 416-3, may each be part of the data hub 416 (e.g., where each ledger forms part of the data hub), although the ledgers are shown with individual lines in FIGS. 8A-8B.

The use of the three blockchain layers for storing a secret device key, a secret member key, and the secret member-device association, allows for three dimensions of security for the sensitive health data streams from the IoT product 404 related to the member 410. For example, the use of the three ledgers may ensure that the proper device is registered to the data hub 416, and that the proper member 410 is using the product 404, prior to storing data from the product 404. If the device is lost, traded in, etc., a different user will not accidentally have their data saved to the data hub 416. In various implementations, the data hub 416 will not only require that members 410 must be valid and registered and that products 404 need to be registered, but the data hub 416 may also require that a given product 404 is specifically linked to a member 410 before any critical data may be accepted from the product 404.

At line 840, clinical data is streamed from the IoT product 404 to the universal data curation platform 412. At line 844, the universal data curation platform 412 checks for a valid member-device association from the blockchain secret member-device association ledger 416-3. If the blockchain secret member-device association ledger 416-3 returns a valid authorization for processing device data at line 848, the universal data curation platform 412 proceeds to standardize and store the data from device stream at line 852. Therefore, the blockchain secret member-device association ledger may not only check that the product 404 is registered and that the member 410 is valid, but also that the given product 404 is associated with the member 410.

The universal data curation platform 412 than supplies structured/curated data to the data hub 416 at line 856, and the data hub supplies data to the analysis engines at line 860. At line 864, the universal data curation platform 412 supplies unclassified data to the data harvester 420, and the data harvester 420 stores the data for later use at line 868. The data harvester 420 may store data similar in a similar manner to the similar to the data hub 416, where the data harvester 420 provides immutable and timestamped recording of the received unclassified data.

Personalized Micro-Engines

Figure 9:
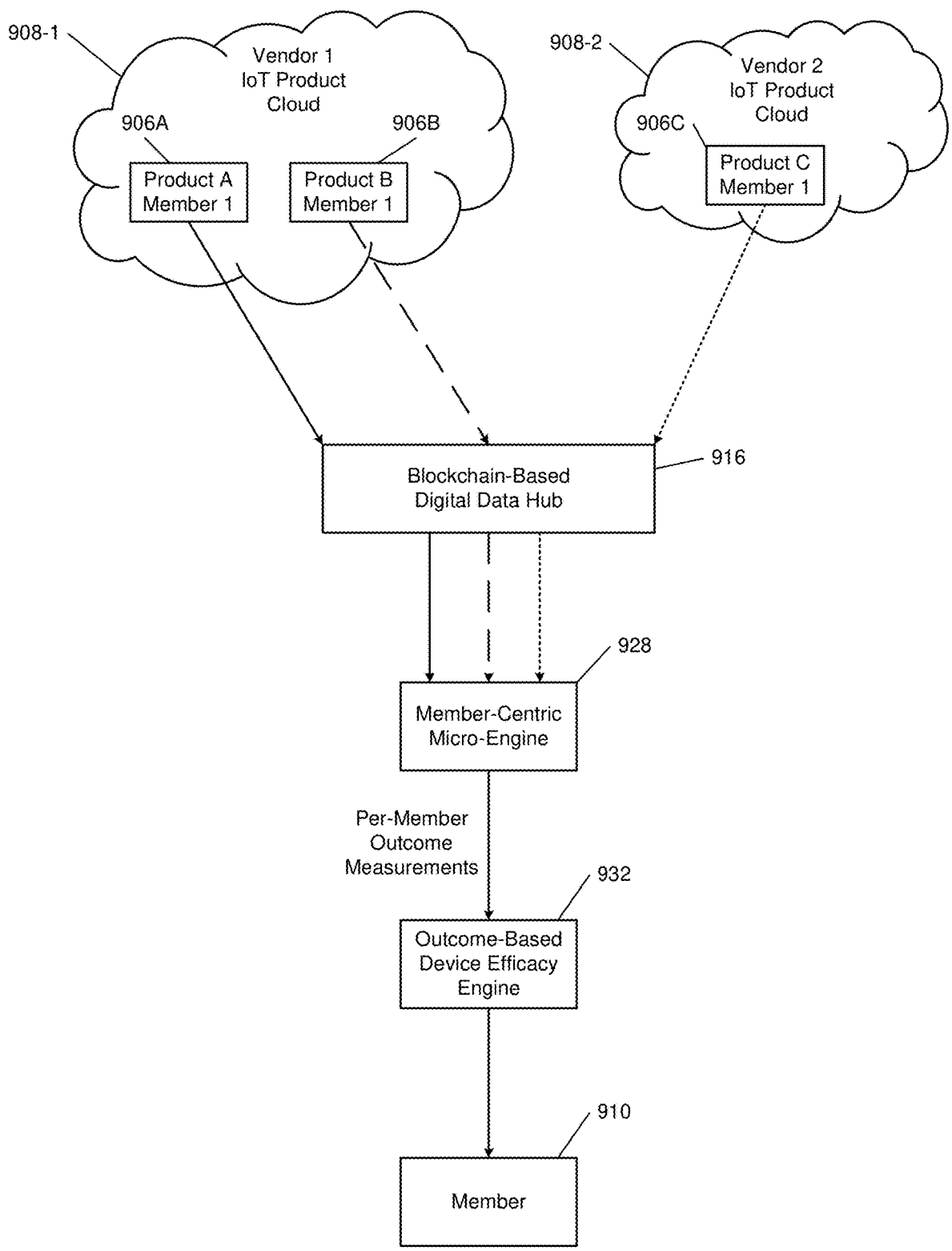
FIG. 9 is a functional block diagram of an example member-centric personalized micro-engine.

FIG. 9 illustrates an example flow of a member-centric micro-engine 928, which may be similar to the personalized micro-engine 428 of FIG. 4. As shown in FIG. 9, an IoT product cloud 908-1 for a first vendor facilitates streaming data from a product 906A of a first member and another product 906B of the first member, to the data hub 916 (which may include standardization via the universal data curation platform 412).

The data hub 916 also receives data from a third product 906C belonging to the first member. The product 906C is from a second vendor, and the IoT product cloud 908-2 of the second vendor may facilitate streaming of data from the product 906C to the data hub 916. In this example, the single member provides streaming data from three different devices (e.g., a fitness tracker, a heart rate monitor, and blood pressure monitor).

The member-centric micro-engine 928 receives all three data streams from the data hub 916. For example, the member-centric micro-engine 928 may set up parallel computation nodes for processing the three data streams, such as a Kubernetes Docker, etc.

The member-centric micro-engine 928 (and/or the data hub 916), may scan incoming data streams for a member ID that corresponds to the member that is being analyzed by the member-centric micro-engine 928. The streams that have a matching member ID are then forwarded or routed to the member-centric micro-engine 928, so that the member-centric micro-engine 928 processes only data of products that correspond to that member.

The member-centric micro-engine 928 then aggregates performance characteristics or outcome measurements of the products corresponding to the member, and transmits these results to the outcome-based device efficacy engine 932. The outcome-based device efficacy engine 932 determines how effective these products are at meeting target goals. For example, the outcome-based device efficacy engine may determine whether each product 906A, 906B and 906C is effective in meeting a target goal of losing weight, reducing blood pressure, encouraging daily activity at a specified threshold, etc.

The outcome-based device efficacy engine 932 than supplies the results to the member 910. Member 910 may review the results to determine which of the products 906A, 906B and 906C is most effective, so that the member 910 can focus on using the most effective products, stop using ineffective products, allocate costs or attention to the products more efficiently, etc. In various implementations, the member-centric micro-engine results may be supplied to client organizations, vendors, etc.

Figure 10:
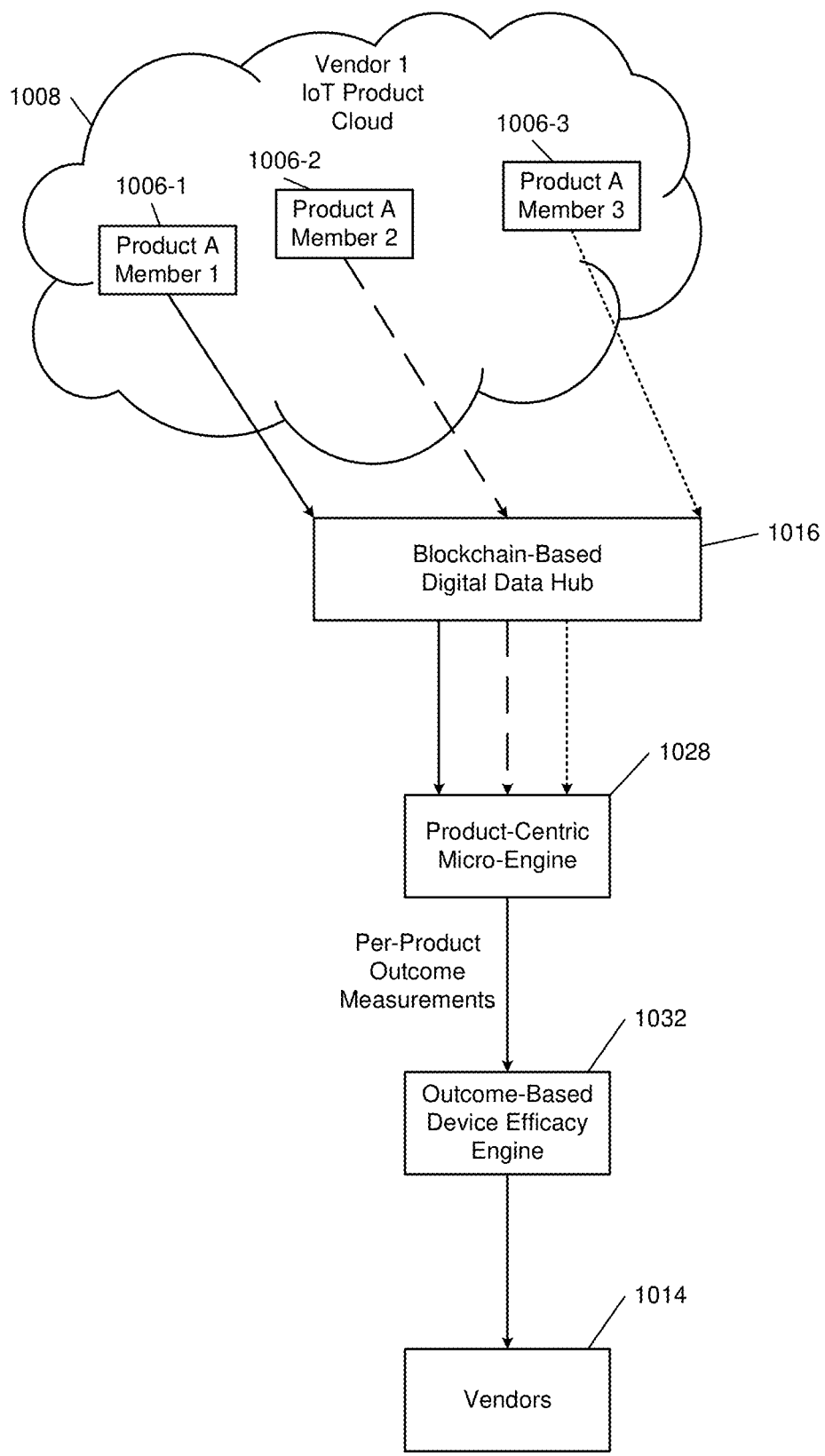
FIG. 10 is a functional block diagram of an example product-centric personalized micro-engine.

FIG. 10 illustrates a flow for an example product-centric micro-engine 1028. The product-centric micro-engine 1028 may be similar to the member-centric micro-engine 928 of FIG. 9, but the product-centric micro-engine 1028 aggregates results of the same product used by multiple members.

As shown in FIG. 10, an IoT product cloud 1008 facilitates streaming of data from three of the same products of the vendor, that each belong to a different member. A first product 1006-1 is used by a first member, a second product 1006-2 is used by a second member, and a third product 1006-3 is used by a third member. Therefore, three different members are all using the same product, and data from each of the products streams to the data hub 1016, which may include standardization from the universal data curation platform 412.

The product-centric micro-engine 1028 receives all three data streams from the data hub 1016. For example, the member the product-centric micro-engine 1028 may set up parallel computation nodes such as a Kubernetes Docker container, etc.

The product-centric micro-engine 1028 (and/or the data hub 1016), may scan incoming data streams for product IDs that correspond to the product that is being analyzed by the product-centric micro-engine 1028. Streams that have a matching product ID are forwarded or routed to the product-centric micro-engine 1028, so that the product-centric micro-engine 1028 processes only data that corresponds to the single specified product (as used by multiple members).

The product-centric micro-engine 1028 aggregates performance characteristics or outcome measurements of the product from the different members, and transmits these results to the outcome-based device efficacy engine 1032. The outcome-based device efficacy engine 1032 determines how effective the products are at meeting target goals across the members. For example, the outcome-based device efficacy engine 1032 may determine that the product is successful on average across members in meeting target goals of losing weight, reducing blood pressure, encouraging daily activity beyond a specified threshold, etc.

The outcome-based device efficacy engine 1032 than supplies results to a vendor 1014, client organization, etc. The vendor 1014 can then focus on marketing the most effective products, improving weaker products, etc. A client organization may use the results to decide which products to continue subscribing to for a program offered by the client organization, may determine how much to pay a vendor based on success or failure of the products in meeting target goals, etc. The product-centric micro-engine 1028 results may also be supplied to members.

In various implementations, the outcome-based device efficacy engines described herein may be used for various financial flows between the client, vendors, members, products, etc. For example, a vendor may supply a product to members or client organizations using a freemium model, where outcomes of the product are updated every billing cycle and any possible remittance is based on performance of the product above a target value. As an example, the vendor may guarantee that a percentage of device usage will reduce ER costs for a client organization on its members. Depending on the outcome, the client organization may pay the vendor according to how much the costs have been reduced.

Savings from using the product may be distributed in any suitable manner. For example, client organizations may increase member retention and growth, and share a percent of cost savings in rebates. Vendors may optimize installation and operational costs of providing their products to additional members, may have increased product growth, may receive a percentage of cost savings to a client organization subscribing to the products, etc.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. The phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module. For example, the client module may include a native or web application executing on a client device and in network communication with the server module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A computerized method of capturing monitor device data in a blockchain, the method comprising:
receiving a product identifier and product registration information for a monitor device supplied by a vendor;
generating a secret device key for the monitor device;
configuring the monitor device with the secret device key;
receiving a member identifier and member registration information for a member associated with the monitor device;

generating, by a blockchain secret member key ledger, a
   secret member key;
linking the secret member key with the monitor device;
receiving, by a blockchain secret member-device association ledger, an associated pair of the secret device key with the secret member key to store the associated pair for further authentication and authorization by the blockchain secret member-device association ledger;
receiving, by a universal data curation platform, a data stream from the monitor device, wherein the data stream includes a device key and a member key;
authorizing the data stream by checking the received device key and the received member key against the blockchain secret member-device association ledger to determine whether a valid association of the monitor device and the member exists; and
in response to a confirmation that the valid association of the monitor device and the member exists:
   standardizing the data stream from the monitor device, and
   storing the standardized data stream in a blockchain.

2. The method of claim 1 wherein generating the secret device key for the monitor device occurs by a blockchain secret device key ledger.

3. The method of claim 2 wherein the blockchain secret device key ledger is implemented by a ledger of a single blockchain.

4. The method of claim 3 wherein:
the blockchain is a first blockchain; and
the method further comprises, in response to the confirmation of the valid association of the monitor device and the member according to the received device key and the received member key and the blockchain secret member-device association ledger:
   identifying non-classified data in the data stream; and
   supplying the identified non-classified data to a second blockchain of an uncultivated data harvester.

5. The method of claim 4 further comprising supplying the standardized data stream from the blockchain to one or more data analysis engines to determine a health status of the member.

6. The method of claim 2 wherein at least two of the blockchain secret device key ledger, the blockchain secret member key ledger, and the blockchain secret member-device association ledger are implemented by a ledger of a single blockchain.

7. The method of claim 2 wherein the blockchain secret device key ledger, the blockchain secret member key ledger, and the blockchain secret member-device association ledger are implemented by a ledger of a single blockchain.

8. The method of claim 2 wherein the blockchain secret device key ledger, the blockchain secret member key ledger, and the blockchain secret member-device association ledger are a part of a data hub configured with role-based access control policies.

9. The method of claim 1 wherein:
the blockchain is a first blockchain; and
the method further comprises, in response to the confirmation of the valid association of the monitor device and the member according to the received device key and the received member key and the blockchain secret member-device association ledger:
   identifying non-classified data in the data stream; and
   supplying the identified non-classified data to a second blockchain of an uncultivated data harvester.

10. The method of claim 1 further comprising supplying the standardized data stream from the blockchain to one or more data analysis engines to determine a health status of the member.

11. A system comprising:
memory hardware configured to store computer-executable instructions; and
processor hardware configured to execute the instructions, wherein the instructions include:
   receiving a product identifier and product registration information for a monitor device supplied by a vendor;
   generating, by a blockchain secret device key ledger, a secret device key for the monitor device;
   configuring the monitor device with the secret device key;
   receiving a member identifier and member registration information for a member associated with the monitor device;
   generating, by a blockchain secret member key ledger, a secret member key;
   linking the secret member key with the monitor device;
   receiving, by a blockchain secret member-device association ledger, an associated pair of the secret device key with the secret member key to store the associated pair for further authentication and authorization by the blockchain secret member-device association ledger;
   receiving, by a universal data curation platform, a data stream from the monitor device, wherein the data stream includes a device key and a member key;
   authorizing the data stream by checking the received device key and the received member key against the blockchain secret member-device association ledger to determine whether a valid association of the monitor device and the member exists; and
   in response to a confirmation that the valid association of the monitor device and the member exists:
      standardizing the data stream from the monitor device, and
      storing the standardized data stream in a blockchain.

12. The system of claim 11 wherein generating the secret device key for the monitor device occurs by a blockchain secret device key ledger.

13. The system of claim 12 wherein the blockchain secret device key ledger includes a ledger of a single blockchain.

14. The system of claim 13 wherein:
the blockchain is a first blockchain; and
the instructions include, in response to confirmation of the valid association of the monitor device and the member according to the received device key and the received member key and the blockchain secret member-device association ledger:
   identifying non-classified data in the data stream; and
   supplying the identified non-classified data to a second blockchain of an uncultivated data harvester.

15. The system of claim 14 wherein the instructions include supplying the standardized data stream from the blockchain to one or more data analysis engines to determine a health status of the member.

16. The system of claim 12 wherein at least two of the blockchain secret device key ledger, the blockchain secret member key ledger, and the blockchain secret member-device association ledger are implemented by a ledger of a single blockchain.

17. The system of claim 12 wherein the blockchain secret device key ledger, the blockchain secret member key ledger, and the blockchain secret member-device association ledger are implemented by a ledger of a single blockchain.

18. The system of claim 12 wherein the blockchain secret device key ledger, the blockchain secret member key ledger, and the blockchain secret member-device association ledger are a part of a data hub configured with role-based access control policies.

19. The system of claim 11 wherein:
the blockchain is a first blockchain; and
the instructions include, in response to confirmation of the valid association of the monitor device and the member according to the received device key and the received member key and the blockchain secret member-device association ledger:
 identifying non-classified data in the data stream; and
 supplying the identified non-classified data to a second blockchain of an uncultivated data harvester.

20. The system of claim 11 wherein the instructions include supplying the standardized data stream from the blockchain to one or more data analysis engines to determine a health status of the member.

\* \* \* \* \*